US00PP33149P3

(12) United States Plant Patent
Hansoti

(10) Patent No.: US PP33,149 P3
(45) Date of Patent: Jun. 8, 2021

(54) ***SANSEVIERIA* 'HANSOTI26'**

(50) Latin Name: *Sansevieria javanica*
Varietal Denomination: HANSOTI26

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 17/011,711

(22) Filed: Sep. 3, 2020

(65) Prior Publication Data

US 2021/0068328 P1 Mar. 4, 2021

(30) Foreign Application Priority Data

Sep. 4, 2019 (QZ) ..... PBR 2019/2154

(51) Int. Cl.
*A01H 5/00* (2018.01)
*A01H 6/12* (2018.01)

(52) U.S. Cl.
USPC ..... Plt./382
CPC ..... *A01H 6/12* (2018.05)

(58) Field of Classification Search
USPC ..... Plt./382
See application file for complete search history.

*Primary Examiner* — Annette H Para
(74) *Attorney, Agent, or Firm* — Cassandra Bright

(57) ABSTRACT

A new and distinct cultivar of *Sansevieria* plant named 'HANSOTI26' is disclosed, characterized by unique light grey-green foliage with distinct dark green linear markings in the form of linear lines along the length of the leaf and transverse cross hatching on this, contrasting with the light green background. The arched leaves are relatively fleshy, strap-like with maximum width up to 3 cm, upright, somewhat stiff with soft, non-aggressive tips that do not hurt or poke even in large mature plants. 'HANSOTI26', unlike most commercial *Sansevieria* cultivars, comes true to type and quickly forms adventitious shoots from leaf cuttings. Plants of 'HANSOTI26' are extremely tough, even when compared to other *Sansevieria* cultivars, and are very long lasting under low light indoor conditions. The new variety is a *Sansevieria*, categorized within the Novelty *Sansevieria* Group, typically produced as an indoor ornamental plant.

5 Drawing Sheets

Latin name of the genus and species: *Sansevieria javanica.*

Variety denomination: 'HANSOTI26'.

BACKGROUND OF THE INVENTION

The present invention relates to a new and distinct cultivar of *Sansevieria* plant, botanically known as *Sansevieria javanica* of the family Asparagaceae, hereinafter referred to by the cultivar name 'HANSOTI26'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI26' was discovered and selected by the inventor, Ashish Hansoti, as a chance seedling from open pollinated seeds on an unpatented, unnamed variety of *Sansevieria* in the inventor's collection labelled as "*Sansevieria javanica*". The pollen parent was unknown (seedling from open pollinated seeds). The open-pollination was performed at a commercial nursery in Village Done, District Thane, Maharashtra State in Western India. The date of this open-pollination cannot be confirmed by the inventor. Selection was made during January of 2009.

Asexual reproduction of the new *Sansevieria* cultivar by vegetative cuttings as well as leaf cuttings was first performed in November 2010 in Village Asle, District Satara, Maharashtra State in Western India and it was seen that the distinctive combination of characteristics of the new cultivar reproduced true However, it was subsequently discovered (sometime in autumn 2015) that the variety 'HANSOTI26' came true even from leaf cuttings. This was a breakthrough as not only did it mean much quicker propagation but also the production of smaller plants which were suitable for smaller pots and also developed a good form when grown for 3-4 months in smaller size pots such as a 12 cm pot.

BRIEF SUMMARY OF THE INVENTION

The following traits have been repeatedly observed and are determined to be unique characteristics of 'HANSOTI26', which in combination distinguish this *Sansevieria* as a new and distinct cultivar:

1. Unique light grey-green foliage with distinct dark green linear markings in the form of linear lines along the length of the leaf and transverse cross hatching on this, contrasting with the light green background. Overall, 'HANSOTI26' presents as a grey-green, slightly stiff foliaged pot plant with contrasting lines of dark green.
2. The arched leaves are relatively fleshy, strap like with maximum width up to 3 cm, upright, somewhat stiff with soft, non-aggressive tips that do not hurt or poke even in large mature plants.
3. 'HANSOTI26', unlike most commercial *Sansevieria* cultivars, comes true to type and quickly forms adventitious shoots from leaf cuttings and the resulting pups can be used in various size pots. In contrast, when grown from side shoots, by the time that the pups attain a rosette form, they are invariably too large for pots of 12 cm of smaller. Typically, 3 Plants per Pot (3PP) are used to give a full-bodied pot plant.

4. Leaves are small in pups and get longer with age. Leaves in plants grown in 9 cm pot would be 15-16 cm long and those in 12 cm pots 23-25 cm long. About 9-12 leaves per plant, increasing in number with plant age.
5. 'HANSOTI26' is extremely tough plant, even when compared to other *Sansevieria* cultivars, with practically no pests or disease problems and very long lasting under low light indoor conditions.

The new variety 'HANSOTI26' is considered a variety of *Sansevieria* in the group denominated as "Novelty *Sansevieria* Group" as in it is not one of the *Sansevieria trifasciata* species. The new variety presents an average of 10 leaves per plant when it reaches sale size (between 2-4 months from rooted liner depending on finished pot size).

The new variety has an upright growth habit and the entire plant can reach a height range between 20 and 25 cm when grown in a 12 cm pot. The leaves are narrow with maximum width of 3 cm and lanceolate with a distinct texture and waxy feel. The blades are somewhat thick or fleshy.

The new variety is moderately drought tolerant and adapts well to conditions of bright light and heavy shade (exterior and interior).

The main color of a recently mature leaf is a green near 138B with darker lines and cross hatching which is near 139A. The underside of the leaf is near 138C. With age the leaf color darkens slightly. Attached colour pictures are a better guide to the overall colouration than written descriptions.

COMMERCIAL COMPARATOR

Plants of the new *Sansevieria* 'HANSOTI26' can be compared to the variety *Sansevieria bacularis* 'Mikado' (unpatented) which is another *Sansevieria* in the "Novelty *Sansevieria* Group" and is propagated and grown in a similar fashion. 'Mikado' has much fleshier, almost terete leaves with a distinct sulcus or groove along the length. In cross section leaves are almost circular with a small sulcus and a maximum diameter of 1 cm. Overall coloration is much darker green with indistinct cross hatching and no linear lines. 'Mikado' is slower growing compared to 'HANSOTI26' in both, speed of propagation and in subsequent growth from Liners to finished pot plant. The table below summarizes the differences:

TABLE I

Comparison of Similar *S. bacularis* 'Mikado' & New variety 'Hansoti26'

| | Characteristic | *S. bacularis* 'Mikado' | New cv 'Hansoti26' |
|---|---|---|---|
| 1. | Leaf Habit | Mikado has much fleshier, almost terete leaves with a distinct sulcus or groove along the length | HANSOTI26 has flatter, only somewhat fleshy leaves. |
| 2. | Leaf Colour | Overall coloration is much darker green with indistinct cross hatching and no linear lines | Overall coloration is much lighter Grey-green |
| 3. | Leaf size & Shape | Leaves are narrower and more recumbent. | Leaves are broader and more upright. |
| 4. | Plant Habit | Mikado is slower growing compared to Hansoti 26 | Hansoti26 is faster growing than 'Mikado' |
| 5. | Plant Vigour | Somewhat less vigorous, taking longer to give pups from leaf cuttings and slower subsequent growth. | Somewhat more vigorous, giving pups from leaf cuttings quicker and also faster subsequent growth. |

PARENTAL COMPARISON

Plants of the new *Sansevieria* 'HANSOTI26' differ from plants of the seed parent in the following characteristics:

1. Foliage of the new variety is thicker than foliage of the seed parent.
2. Foliage of the new variety has a unique cross-hatch variegation not found in foliage of the seed parent variety.

BRIEF DESCRIPTION OF THE PHOTOGRAPHS

The accompanying photographs illustrate the overall appearance of the new *Sansevieria* cultivar 'HANSOTI26' showing the colors as true as is reasonably possible with colored reproductions of this type. Colors in the photographs may differ slightly from the color value cited in the detailed botanical description which accurately describe the color of 'HANSOTI26'.

These pictures illustrate the plant form which is the unique characteristic of 'HANSOTI26'. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

DETAILED BOTANICAL DESCRIPTION

Figure 1:
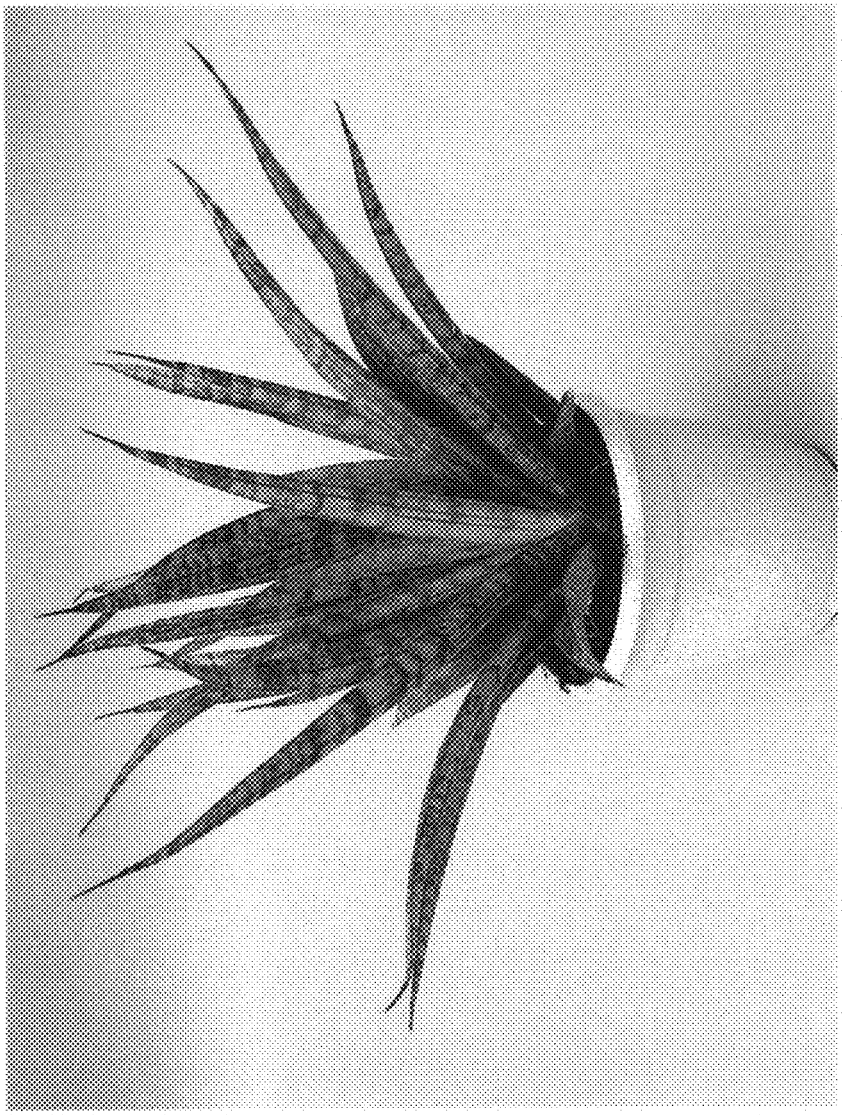
FIG. 1 illustrates a three-month-old plant of *Sansevieria* 'HANSOTI26' in a 12 cm diameter pot.
Figure 2:
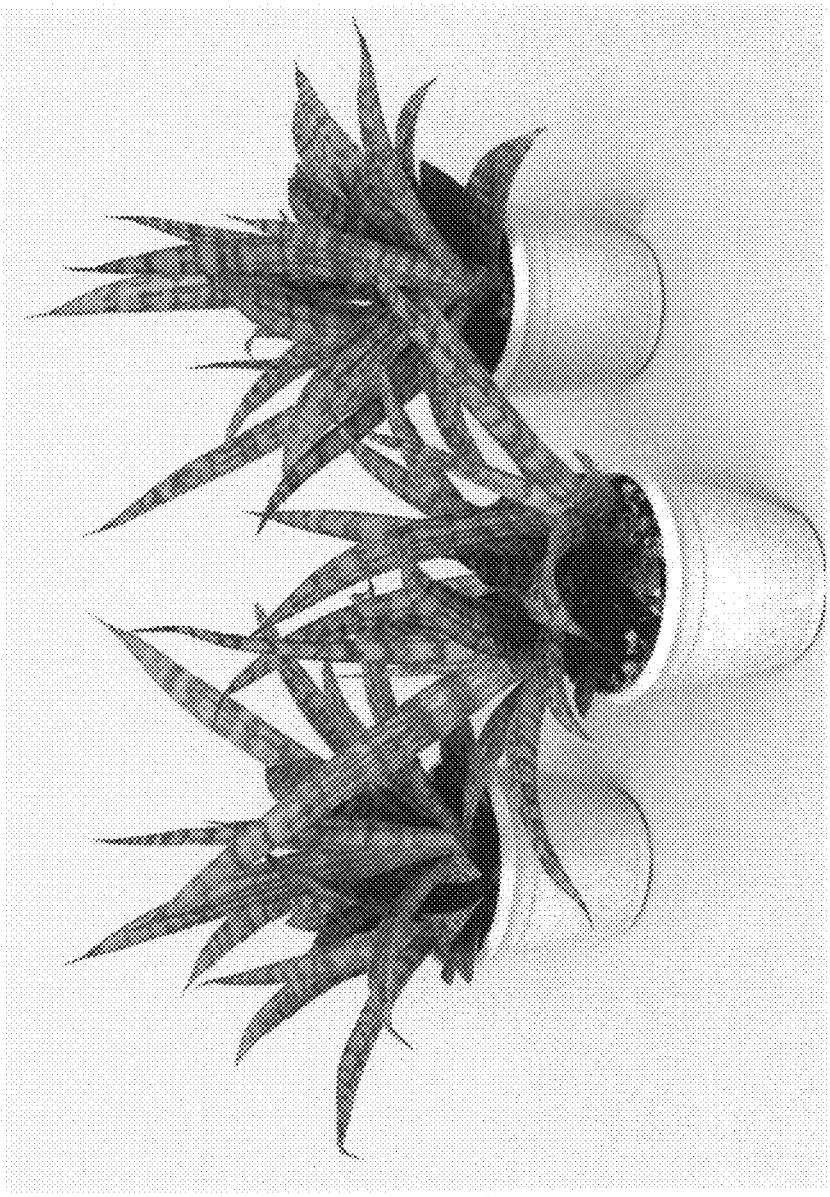
FIG. 2 illustrates a top view of the plant of 'HANSOTI26' in FIG. 1, showing clearly the grey-green colour and darker lines.
Figure 3:
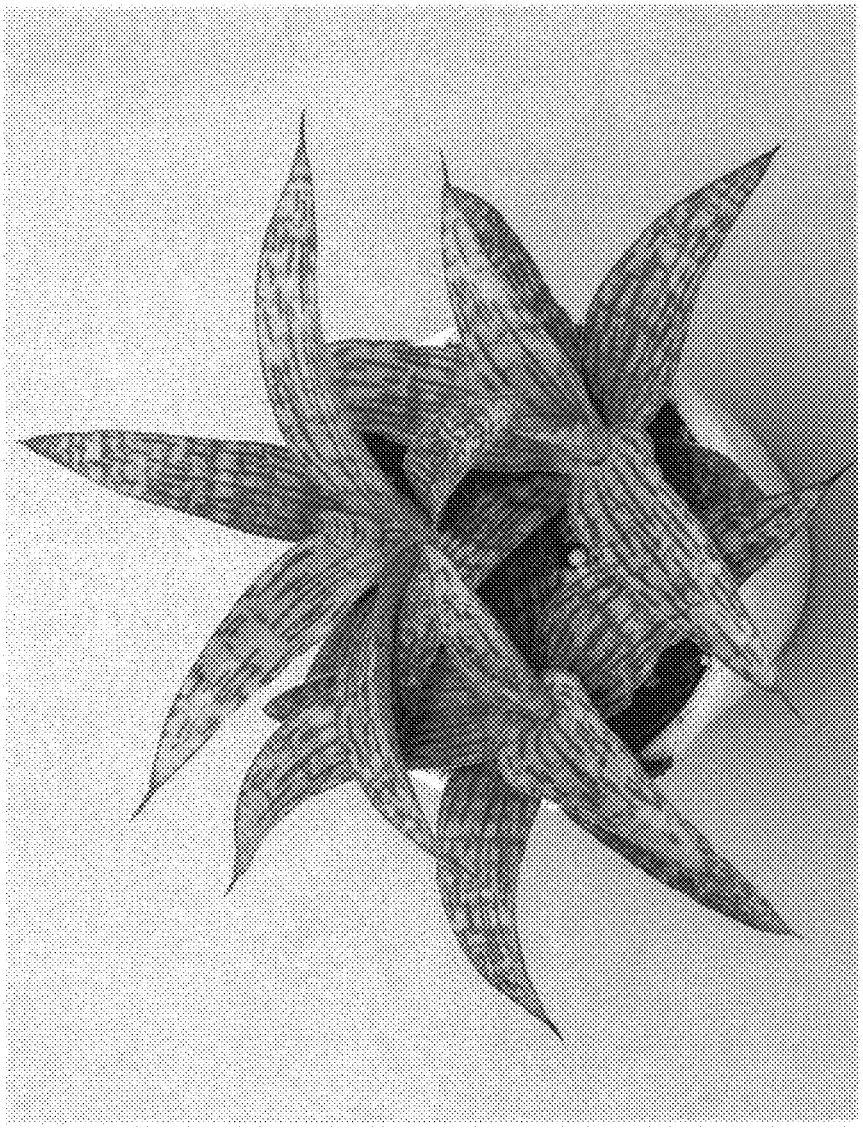
FIG. 3 shows a pot with somewhat juvenile plants of 'HANSOTI26' plants in a 12 cm pot, showing the grey-green colour and darker lines.
Figure 4:
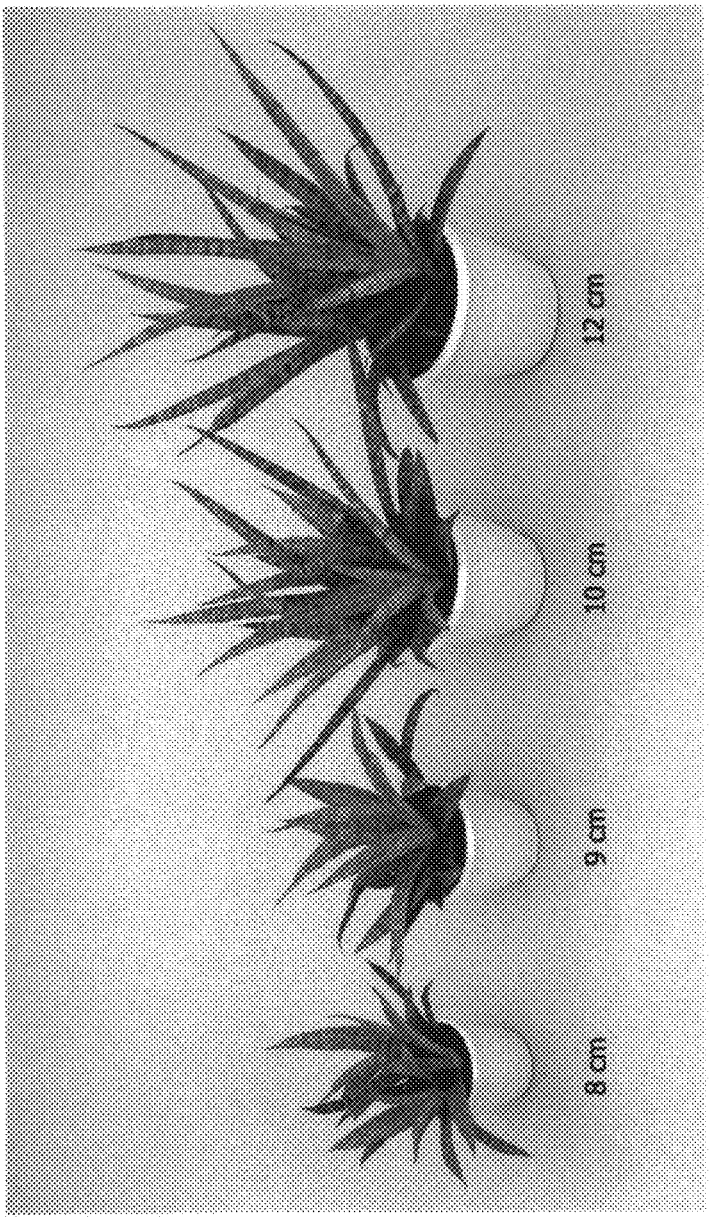
FIG. 4 illustrates 'HANSOTI26' in various pot sizes to show progression and ability of adventitious shoots from leaf cuttings to be used at even rather small pot sizes. Unlike side shoots, adventitious shoots start giving rosettes with good form at a very small size.
Figure 5:
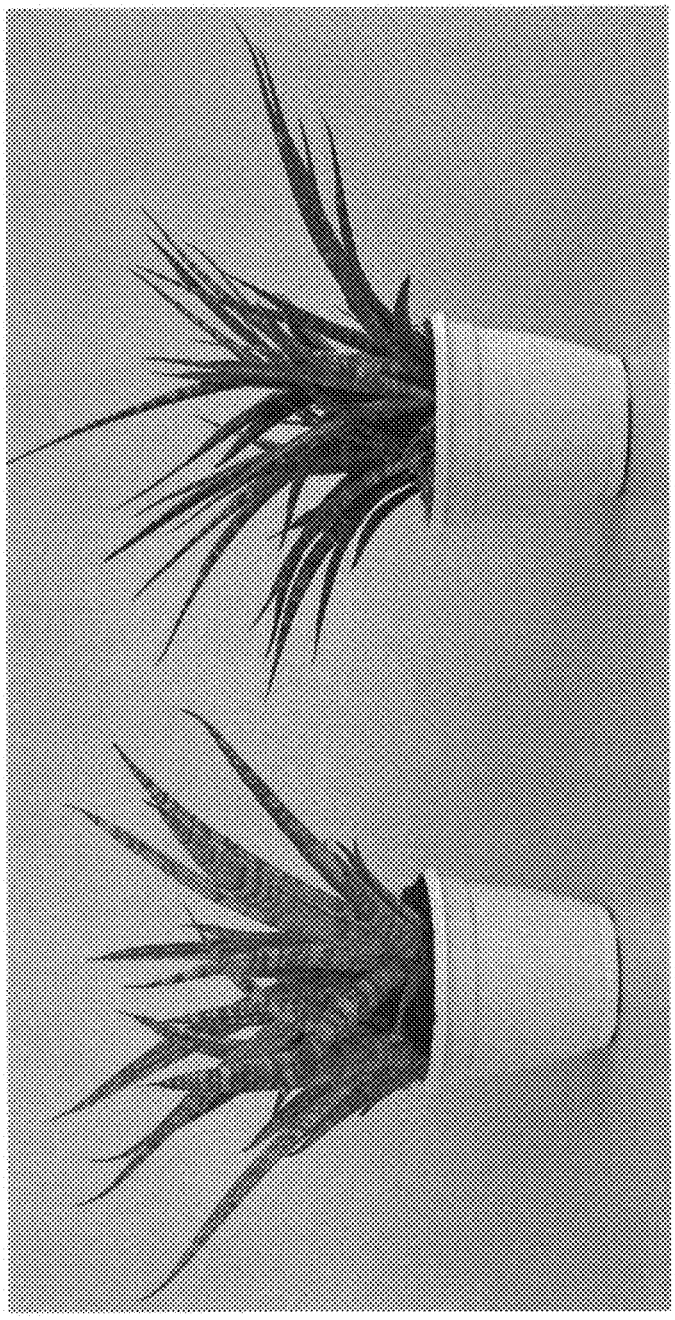
FIG. 5 shows a plant of 'HANSOTI26' (on left) side by side with a plant of closest comparable cultivar, a plant of *Sansevieria bacularis* 'Mikado', both in 12 cm pots. The cultivar 'Mikado' lacks the distinct grey-green colour and the darker lines of 'HANSOTI26' and has much more cylindrical or terete, dark green leaves. 'HANSOTI26' is on the left in the photo.

The new *Sansevieria* 'HANSOTI26' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI26' plants grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions).

This crop gets nearly constant fertilization to increase production, Constant Liquid Feed at approximately 150 ppm N, 30 ppm P and 150 ppm K is used along with micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the Winter season in Asle, District Satara, Maharashtra State, India when outdoor day temperature was 25° C. to 30° C. The age of the plants described is 3 to 4 months.

Botanical classification: *Sansevieria javanica* 'HANSOTI26'.

General information:

*Optimal growth conditions.*—

*Light intensities.*—High adaptability to outdoor or indoor conditions.

*Temperature.*—Day: 25° C. to 35° C. Night: 12° C. to 25° C.

*Temperature tolerance.*—Tolerant to a low temperature of about 8° C. and a high temperature of 38° C. and above, very heat tolerant.

*Fertilization.*—Constant feed of 150 ppm N, 30 ppm P and 150 ppm K is used along with micronutrients with occasional leaching.

*Growth regulators.*—Not necessary for growth, however rooting hormone aids in rapid and prolific rooting of offsets.

Propagation:

*Typical.*—Vegetative, by leaf cuttings — unlike most *Sansevieria* cultivars, 'HANSOTI26' comes true from leaf cuttings. Propagation using side shoots or suckers also possible.

*Rooting habit and description.*—Rhizomes are elongated, fleshy, giving rise to offsets (side shoots). Offsets root easily with fibrous adventitious roots from cut end. Colored cream to brown, not accurately measured with R.H.S. chart.

*Time to initiate roots.*—30 to 40 days at 25 to 30° C.

*Time to produce a rooted liner.*—About 60 to 75 days at 25° C. to 30° C.

*Time to produce a sales ready* 12 *cm potted plant from liner.*—About 3 months at 25° C. to 30° C.

Plant:

*General appearance and form.*—Upright, outer rosette foliage reflexed and recumbent.

*Height.*—About 15 cm to 20 cm when grown in 12 cm pots.

*Spread.*—About 25 cm to 30 cm when grown when grown in a 12 cm size container.

*Form.*—Monocot; leaf bases arranged in a rosette around growth point.

*Shape.*—Inverted triangle.

*Growth rate.*—Rapid.

Foliage:

*Quantity.*—About 9 to 12 in a 12 cm, ready to sell plant. Increases with age.

*Arrangement.*—Rosulate.

*Leaf length.*—About 20 cm to 30 cm, in a 12 cm pot, full mature leaf 100 cm to 120 cm.

*Leaf width.*—About 2.5 cm to 3.0 cm.

*Overall shape of leaf.*—Lanceolate.

*Aspect.*—Slightly to moderately undulate.

*Apex shape.*—Aristate but soft and safe to touch. Not particularly brittle so plants not easily damaged on handling.

*Base shape.*—Decurrent.

*Margin.*—Entire. Entire.

*Texture.*—Upper Surface: Smooth and waxy texture.

*Texture.*—Under Surface: Smooth and waxy texture.

*Pubescence.*—None.

*Color.*—Upper surface mature leaf: Basal color near Green 138B with darker lines and cross hatching near 139A. Lower surface mature leaf: Basal color near Green 138C with darker lines and cross hatching near 139A. Lower surface nearer 138C. Margin coloration: Near RHS Green 136A upper and lower surfaces. Young foliage near Yellow-Green 144D.

*Venation.*—Pattern: Longitudinal/parallel leaf shape.

*Venation color.*—Indistinguishable from leaf blade.

*Leaf fragrance.*—None.

Other:

*Inflorescence description.*—Flowers not observed to date.

*Weather resistance.*—Moderately drought tolerant.

*Pest resistance.*—Reasonably resistant to pests, susceptible to root mealybugs.

*Disease resistance.*—Occasionally shows Anthracnose and leaf spots but largely disease free from clean mother stock.

*Fruit/seed production.*—No fruits/seeds detected to date.

What is claimed is:

1. A new and distinct cultivar of *Sansevieria* plant named 'HANSOTI26' as herein illustrated and described.

* * * * *